United States Patent [19]

Chaudhuri et al.

[11] Patent Number: 5,011,941

[45] Date of Patent: Apr. 30, 1991

[54] QUATERNIZED NITROGEN CONTAINING COMPOUNDS

[75] Inventors: Ratan K. Chaudhuri, Butler; David J. Tracy, Lincoln Park; Robert B. Login, Oakland, all of N.J.

[73] Assignee: GAF Chemicals Corporation, Wayne, N.J.

[21] Appl. No.: 582,289

[22] Filed: Sep. 14, 1990

Related U.S. Application Data

[62] Division of Ser. No. 370,226, Jun. 22, 1989.

[51] Int. Cl.$^5$ .................. C07D 207/12; C07D 211/76; C07D 295/12
[52] U.S. Cl. .................................... 548/550; 546/243; 540/451; 540/531
[58] Field of Search ............... 548/550; 546/243; 540/451, 531

[56] References Cited

U.S. PATENT DOCUMENTS 4,732,990  3/1988  Login et al. .................. 548/550
4,885,158  12/1989  Tracy et al. .................. 514/424

Primary Examiner—David B. Springer

Attorney, Agent, or Firm—Marilyn J. Maue; Joshua J. Ward

[57] ABSTRACT

The invention relates primarily to quaternized compounds having the formula

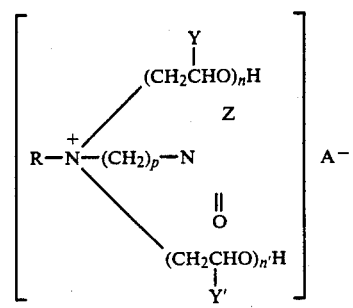

wherein n and n' are each independently integers having a value of from 1 to 25; p is an integer having a value of from 1 to 4; Y and Y' are each independently H or $CH_3$; R is linear alkyl, alkenyl, or amidoalkyl having from 8 to 22 carbon atoms and is optionally substituted with $C_1$ to $C_4$ alkyl; Z is linear alkylene having from 3 to 8 carbon atoms and is optionally substituted with lower alkyl and $A^-$ is an anion.

4 Claims, No Drawings

QUATERNIZED NITROGEN CONTAINING COMPOUNDS

This is a division of application Ser. No. 370,226, filed June 22, 1989.

In one aspect the invention relates to novel quaternized compounds which possess emulsifying, dye leveling, antistatic and fabric softening properties. In another aspect the invention relates to novel quaternized compounds having high compatability with anionic and non-ionic components widely used in the formulation of cosmetic compositions such as hair and skin care compositions. Still another aspect of the invention relates to the preparation of said quaternized compounds and in still another aspect, the invention relates to the use of said compounds in several fields of application.

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Problems arise from the limited compatibility of anionic detergents with commercial cationic conditioning agents which precipitate out of solution in shampoo formulations.

Shampoo formulations have employed conventional anionic surfactants such as sodium lauryl sulfate, ammonium lauryl sulfate, ammonium lauryl ether sulfate and sodium lauryl ether sulfate which have been found to be incompatible with most cationic conditioning agents at effective concentration levels.

Additionally, reproducible emulsifying media for polymerizations requiring product molecular weight control is often very difficult to achieve.

Accordingly it is an object of this invention to minimize or obviate the above problems while providing additional benefits in hair and skin treating formulations.

Another object of the invention is to provide novel quaternized nitrogen containing compounds having unique properties, particularly fabric softening and antistatic properties.

Another object is to provide novel quaternized nitrogen containing compounds having excellent hair or skin conditioning properties when incorporated into a shampoo or skin lotion and having high compatibility with components of hair and skin treating formulations.

Another object is to provide an economical and commercially feasible method for the preparation of said novel quaternized nitrogen containing compounds.

Still another object is to provide processes for the use of said quaternized compounds.

These and other objects will become apparent from the following description and disclosure.

THE INVENTION

According to this invention there is provided quaternized compounds having unique properties and defined by the formula

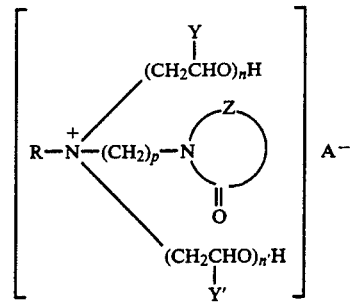

wherein n and n' are each independently integers having a value of from 1 to 25; p is an integer having a value of from 1 to 4; and Y' are each independently H or $CH_3$; R is linear alkyl, alkylene or amidoalkyl having from 8 to 22 carbon atoms and is optionally substituted with $C_1$ to $C_4$ alkyl; Z is linear alkylene having from 3 to 8 carbon atoms and is optionally substituted with lower alkyl and $A^-$ is an anion. The anion can be a chloride, bromide, iodide, sulfite, sulfate or sulfonate.

Preferred compounds within the above group are those wherein p is 1; R is a tallow or coco moiety and Z is unsubstituted propylene or butylene. Examples of the pyrrolidonyl compounds of this invention include:

Bis-(2-hydroxyethyl) [(2-pyrrolidonyl)methyl] tallow ammonium salt

Bis-[2(2-hydroxyethoxy)ethyl] [2-pyrrolidonyl)methyl] tallow ammonium salt

Bis-(2-hydroxypropyl) [(2-pyrrolidonyl)methyl] coco ammonium salt

Bis-[2(2-hydroxypropoxy)propyl] [(2-pyrrolidonyl)ethyl] coco ammonium salt

Bis-hydroxyethoxylated quaternary of [(2-pyrrolidonyl)methyl] tallow amine

Bis-hydroxypropoxylated quaternary of [(2-pyrrolidonyl)methyl] tallow amine

Bis-hydroxyethoxylated quaternary of [(2-pyrrolidonyl)methyl] coco amine

Bis-hydroxypropoxylated quaternary of [(2-pyrrolidonyl)methyl] coco amine

Bis-hydroxyethoxylated quaternary of [(2-pyrrolidonyl)methyl] dodecyl amine

Bis-hydroxyethoxylated quaternary of [(2-pyrrolidonyl)methyl] octadecyl amine

Bis-hydroxyethoxylated quaternary of [3(2-pyrrolidonyl)propyl] tetradecyl amine

Bis-hydroxyethoxylated quaternary of [2(2-pyrrolidonyl)ethyl] octadecyl amine

It will be understood that compounds containing heterocyclic rings other than the pyrrolidonyl radical can be substituted in the above named compounds. Hence the corresponding piperidonyl, azacycloheptanonyl, azacyclononanonyl and azacyclodecanonyl equivalents of the above compounds are included within the scope of this invention.

The present quaternary compounds possess unique properties, among which is their ability to form emulsions in the polymerization of acrylates. As additives in hair and skin conditioning formulations the present products provide softening, antistatic and moisturizing properties and possess high compatibility with anionic surfactants. In the context of this application, "conditioning" includes the functions of moisturizing, softening, cleansing, penetrating, disinfecting, luster enhancing, hair combability, thickening, dye retention and others. These compounds are highly compatible with α-olefin sulfonates and anionic surfactant salts conventionally employed in shampoos, skin lotions and textile treating products. Their compatibility is such that up to 5% by weight or more of the quaternized compounds can be incorporated in the formulation, a characteristic which permits the formation of effective formulations as liquids or gels. In contrast, most prior quaternary viscosity building conditioning compounds are incorporable only up to 0.5 or 1 wt. percent based on total anionic formulations. It is contemplated that mixtures of the present quaternized compounds employed in shampoos, hair conditioners, skin lotions and textile treating compositions as an agent which incorporates softening, thickening, scroop, conditioning and emulsifying qualities in one additive; thus eliminating the need for separate chemical components to accomplish these individual needs. The present compounds may also be used as dye levelors and penetrating agents in the treatment of fabrics or pelts. In applications, the quaternary compounds of this invention are generally mixed with a standard formulation of in an effective amount which can range from between about 0.05 to about 15% by weight, preferably between about 0.5 and about 8% by weight, of the total formulation. The compatability of the present compounds with anionic α-olefin sulfonates is surprising since most anionic compounds cause precipitation of cationic agents. However, the present compounds in concentrations up to 5% by weight show no tendency to precipitate after extended periods including periods up to 6 months or more.

The quaternary pyrrolidonyl compounds of this invention are prepared by an economically feasible process which involves the reaction between an alkyl amine containing at least 8 carbon atoms and a N-haloalkyl lactam having a 5 to 10 membered ring. A general equation for the preparation is defined by the equation:

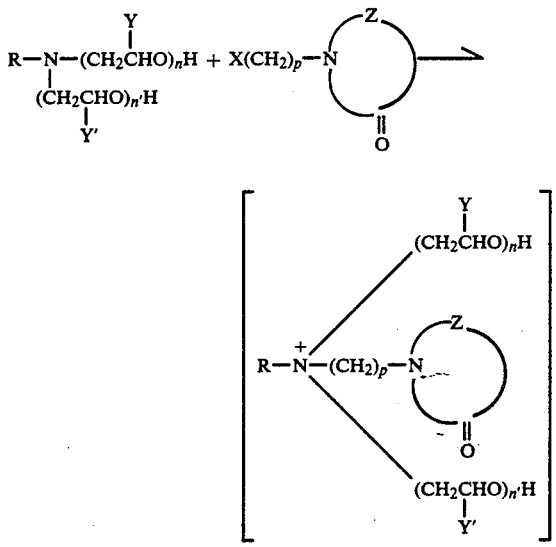

wherein n, n', p, R, Y, Y' and Z are as defined above, X is chloro, bromo or iodo and $X^-$, derived from the haloalkyl pyrrolidone, can be ion exchanged with a tosylate or other sulfate or sulfite ion exchange compound to provide any of the aforementioned anion salts.

Examples of suitable lactam reactants include the N-chloromethyl, N-bromomethyl and N-iodomethyl derivatives of 2-pyrrolidone, 4-methyl-2-pyrrolidone, 4-butyl-2-pyrrolidone, 2-piperidone, methyl-2-piperidone, 2-azacycloheptanone, 2-azacyclooctanone, 2-azacyclononanone, 2-azacyclodecanone and other $C_1$ to $C_4$ alkyl substituted derivatives bonded to an alkylene group in the heterocyclic ring of these lactams. Mixtures of these lactam reactants can also be employed to provide a correspondingly mixed quaternary product, if desired. Of these lactam reactants the N-halomethyl-2-pyrrolidones and N-halomethyl caprolactams are preferred and the N-chloromethyl lactams are most preferred.

The tertiary alkyl diether amines employed in the present process include $C_8$ to $C_{18}$ alkyl ethoxylated or propoxylated species corresponding to the above product formula. The following 2 to 25 moles polyethoxylated or polypropoxylated amines are used: coco amine, tallow amine, decyl amine, dodecyl amine, tetradecyl amine, hexadecyl amine, octadecyl amine etc.

The process is effected under anhydrous conditions by reacting the tertiary alkyl ether amine and the haloalkyl lactam within a critical temperature range of between about 30° and 85° C. preferably between about 40° and about 55° C., under a pressure of from about 0 to about 50 psig, preferably atmospheric pressure, for a period up to about one hour; although usually not more than 30 minutes is required to complete the reaction. The temperature of reaction is closely controlled since the reaction is exothermic and, above 85° C., the product decomposes to form olefinic fatty acid by-products which are difficult and costly to remove.

From the above equation, it is seen that stoichiometric amounts of haloalkyl lactam and tertiary amine are used in the reaction. However, an excess of one or the other of the components is practicable in the process. Generally, for economic considerations, a mole ratio of between 1:1.5 and about 1.5:1 is employed; although, a slight excess of the tertiary amine is recommended to insure complete reaction of the lactam. Accordingly, the most preferred mole ratio of lactam to amine is about 1:1.01 and about 1:1.03.

It is also recommended that the haloalkyl lactam be added gradually or dropwise to the amine at the beginning of the exothermic reaction. At the completion of the reaction, the solid or viscous quaternized product is recovered. Since the reaction is quantitative, the product can be used as is or, when a slight excess of the amine is employed, it can be neutralized with a weak acid such as acetic, lactic or citric acid, depending on the ultimate use of the product.

For incorporating into a standard formulation of shampoo, cream rinse, hand or body lotion, dye bath or textile treating formulation, etc., the present product can be diluted with an inert diluent such as water, propylene glycol, ethanol, etc. The solution in the desired concentration can then be mixed into the formulation to provide a homogeneous liquid, gel, cream or lotion. However, since the present products in solvents are generally liquid at room temperature, they may be directly incorporated into a formulation. Incorporation of the present product is usually affected at room temperature under atmospheric pressure and requires no special formulating technique. However, for certain formulations incorporation of the present product can be effected at temperatures up to about 85° C. and below the decomposition temperature of the product. Amphoteric-containing shampoo formulations are best prepared by initially preparing an aqueous solution of the quaternized product and the amphoteric surfactant and then adding the solution to the shampoo or skin treating formulation.

Having generally described the invention, reference is now had to the accompanying examples which set forth preferred embodiments, but which are not to be construed as limiting to the scope of the invention as more broadly set forth above and in the appended claims.

EXAMPLE 1

To a 1-liter, 4-neck flask equipped with mechanical stirrer, reflux condenser, thermometer, and dropping funnel is added bis-[hydroxyethyl] tallow amine (87.1 g, 0.253 mole) which is heated with stirring to 40° C. under $N_2$ blanket after which the heating source is removed and N-chloromethyl-2-pyrrolidone (33.4 g, 0.25 mole) is added to the amine dropwise over a period of 10 minutes. An exothermic reaction ensues and is controlled to between 70°–80° C. by the rate of addition of N-chloromethyl-2-pyrrolidone. The reaction mixture becomes viscous during the addition of the N-chloromethyl-2-pyrrolidone and remains as a viscous liquid on completion of the reaction. The yield of liquid bis(2-hydroxyethyl) [(2-pyrrolidonyl)methyl] tallow ammonium chloride is quantitative. The content of quaternized product is determined by titration. (Mercuric Acetate method as described by Sidney Siggia, "Quantitative Organic Analysis via Functional Group", 1963, 3d Ed., John Wiley & Sons, pages 552–554).

EXAMPLES 2–7

Example 1 is repeated except that the amines noted in following Table I are substituted for N,N-di(hydroxyethyl) tallow amine. The results of these synthesis reactions are as shown in Table I.

TABLE I

| Example | Amine | Moles of EO* in the Amine | Moles of Poly Ethoxylated Amine | Moles of lactam | % Yield |
|---|---|---|---|---|---|
| 2 | Tallow | 5 | 0.505 | 0.5 | 99 |
| 3 | Tallow | 10 | 1.01 | 1 | 98.5 |
| 4 | Tallow | 20 | 1.01 | 1 | 98 |
| 5 | Coco | 2 | 0.505 | 0.5 | 99.5 |
| 6 | Coco | 10 | 0.505 | 0.5 | 99.5 |
| 7 | Coco | 10 | 0.505 | 0.5 | 98.5 |

*EO = ethylene oxide

EXAMPLE 8

The reaction of Example 1 is repeated except that the amine used is polyethoxylated (5 moles) dodecyl amine (2% molar excess with respect to N-chloromethyl-2-pyrrolidone). The product, bis-hydroxyethoxylated (5 moles) quaternary chloride of [(2-pyrrolidonyl)methyl] dodecyl amine is neutralized with acetic acid and recovered in quantitative yield.

EXAMPLE 9

The reaction of Example 1 is repeated except that the polyethoxylated (10 moles) octadecyl amine and N-chloromethyl-2-piperidone is substituted for bis-hydroxyethyl) tallow amine and N-chloromethyl-2-pyrrolidone. The corresponding bis-hydroxyethoxylated (10 moles) quaternary chloride of [(2-piperidonyl)-methyl] octadecyl amine product is recovered in substantially quantitative yield.

EXAMPLE 10

The quaternized ammonium chloride product of Example 1 (49.0 g) is reacted with p-toluene sulfonic acid sodium salt (19.4 g) for 1 hour at 50° C. The corresponding p-toluene sulfonate salt was recovered in 95% yield.

EXAMPLE 11

| SHAMPOO FOR OILY HAIR | |
|---|---|
| Ingredients | Parts by Weight |
| Compound No. 2 in Table I | 4.0 |
| tetrasodium ethylenediamine tetra-acetic acid | 0.2 |
| sodium lauryl sulfate | 20.0 |
| alpha-olefin sulfonate | 20.0 |
| polyquaternium 11 | 0.5 |
| deionized water | qs |
| preservative | qs |
| colorant | qs |
| fragrance | qs |
| added inorganic salts as desired for viscosity modification | |

EXAMPLE 12

| HAIR CONDITIONER | |
|---|---|
| Ingredients | Parts by Weight |
| Compound No. 3 in Table I | 4.0 |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid to pH | 4 |
| deionized water | qs |
| preservative | qs |
| fragrance | qs |

EXAMPLE 13

| CONDITIONING SHAMPOO | |
|---|---|
| Ingredients | Parts by Weight |
| Compound 6 in Table I | 3.0 |
| N-dodecyl-2-pyrrolidone | 0.6 |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | qs |
| colorant | qs |
| fragrance | qs |

The compounds employed in the formulations of Examples 11–13 provided a significant softening effect on the hair and improved glossiness.

EXAMPLE 14

| MOISTURIZING LOTION | |
|---|---|
| Ingredients | Parts by Weight |
| Compound No. 5 in Table I | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |

-continued

MOISTURIZING LOTION

| Ingredients | Parts by Weight |
| --- | --- |
| Oleth-20*** | 1.0 |
| triethanolamine 98% | 1.0 |
| deionized water | qs |
| preservative | qs |
| fragrance | qs |

*a mixture of methylated siloxane polymers end-blocked with trimethyl siloxy units (dimethylpolysiloxane)
**cross-linked polymer of acrylic acid
***PEG-ether of oleyl alcohol

What is claimed is:

1. The process of synthesizing the compound having the formula

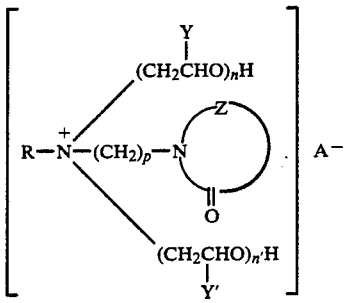

wherein n and n' are each independently integers having a value of from 1 to 25; p is an integer having a value of from 1 to 4; Y and Y' are each independently H or $CH_3$; R is linear alkyl, alkenyl, or amidoalkyl having from 8 to 22 carbon atoms and is optionally substituted with $C_1$ to $C_4$ alkyl; Z is linear alkylene having from 3 to 8 carbon atoms and is optionally substituted with lower alkyl and $A^-$ is an anion which comprises reacting under anhydrous conditions a N-haloalkyl lactam of the formula

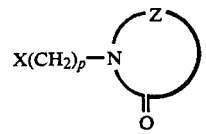

with a slight excess of a tertiary amine having the formula

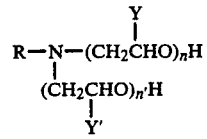

wherein p, Z, R, Y, Y', n and n' are as defined and X is a halogen atom; said reaction being carried out under a pressure of from about 0 to about 50 psig and at a temperature not in excess of 85° C. to produce the corresponding addition product as a quaternized ammonium halide and optionally reacting said quaternized ammonium halide with a sulfate or sulfonate ion exchange agent to provide the corresponding sulfate or sulfonate salt.

2. The process of claim 1 wherein the reaction temperature is between about 40° C. and about 55° C.

3. The process of claim 1 wherein said haloalkyl lactum is N-chloromethyl-2-pyrrolidone.

4. The process of claim 1 wherein n and n' in said tertiary amine each have a value of from 2 to 20 and R is a tallow or a coco radical.

* * * * *